(12) United States Patent
Avinash et al.

(10) Patent No.: US 7,050,615 B2
(45) Date of Patent: May 23, 2006

(54) TEMPORAL IMAGE COMPARISON METHOD

(75) Inventors: Gopal B. Avinash, New Berlin, WI (US); John M. Sabol, Sussex, WI (US); Vianney Pierre Battle, Milwaukee, WI (US); Kadri Nizar Jabri, Waukesha, WI (US); Renuka Uppaluri, Pewaukee, WI (US)

(73) Assignee: GE Medical Systems Glogal Technology Company, LLC, Waukesha, WI (US)

( * ) Notice: Subject to any disclaimer, the term of this patent is extended or adjusted under 35 U.S.C. 154(b) by 725 days.

(21) Appl. No.: 10/064,551

(22) Filed: Jul. 25, 2002

(65) Prior Publication Data

US 2004/0017935 A1     Jan. 29, 2004

(51) Int. Cl.
*G06K 9/00*     (2006.01)
(52) U.S. Cl. .................... 382/131; 382/171; 378/21
(58) Field of Classification Search ........ 382/128–133, 382/154, 169–172, 177, 179, 190, 201, 209, 382/219, 225, 260, 274, 277, 285, 291–297, 382/305; 600/410, 419; 378/21, 23
See application file for complete search history.

(56) References Cited

U.S. PATENT DOCUMENTS

| 5,827,187 | A | * | 10/1998 | Wang et al. | 600/419 |
| 5,873,825 | A | * | 2/1999 | Mistretta et al. | 600/411 |
| 6,064,770 | A | * | 5/2000 | Scarth et al. | 382/225 |
| 6,363,163 | B1 | * | 3/2002 | Xu et al. | 382/130 |
| 6,560,371 | B1 | * | 5/2003 | Song et al. | 382/240 |
| 6,909,797 | B1 | * | 6/2005 | Romsdahl et al. | 382/131 |

* cited by examiner

*Primary Examiner*—Sanjiv Shah
*Assistant Examiner*—Seyed Azarian
(74) *Attorney, Agent, or Firm*—Peter J. Vogel

(57) ABSTRACT

A temporal image processing system includes a temporal processing controller receiving a first image signal and a second image signal from a scanning unit. The temporal processing controller includes a segmentation module, which isolates at least one region of interest between at least two image signals and generates therefrom a segmentation signal. The temporal processing controller also includes a registration module, which receives the segmentation signal and registers the region of interest and generates therefrom a registration signal. The temporal processing controller still further includes a comparison module, which receives the segmentation signal and the registration signal. The comparison module generates therefrom an adaptive comparison signal of the image signals.

18 Claims, 4 Drawing Sheets

TEMPORAL IMAGE COMPARISON METHOD

BACKGROUND OF INVENTION

The present invention relates generally to imaging systems and more particularly to a method to improve the display of temporal changes. Imaging devices, such as x-ray machines, are widely used in both medical and industrial applications. Imaging devices often use temporal processing to track change in an object over time.

Temporal processing systems typically include the following general modules: acquisition storage module, segmentation module, registration module, comparison module, and reporting module. The input images are 1-D, 2-D, 3-D, derived, synthesized, or montaged, where multiple separate images from a single time point are combined to provide a larger composite, seamless image.

Detection of change in medical images of a patient, which are acquired at two different instances in time, has great potential for improving diagnosis. The advent of digital imaging allows computer-assisted detection and identification of these changes and the creation of a "dissimilarity image" containing the change information. This dissimilarity image can be read by a human controller or can become the input to an automated analysis device such as a CAD (computer assisted diagnosis) algorithm.

Currently, as part of Mitsubishi Space Software's "temporal subtraction" application, dissimilarity images are calculated using a simple pixel-by-pixel subtraction of registered images. Simple subtraction, however, results in images with poor contrast, and is not substantially robust when the two initial images are acquired using different techniques.

For a temporal subtraction image, the resulting pixel values (and hence the displayed gray-levels) are proportional to the difference or dissimilarity in pixel value between two input images acquired with temporal separation.

Input images are often registered and processed to compensate for several factors such as: the difference in positioning of the subject during the two image the difference in acquisition parameters, the difference in the bit resolution of the images, and the differences in any pre or post processing that may have been applied to the images.

Image comparison is a common task in a number of applications including temporal processing of mono-modality images (1-D, 2-D, 3-D, derived, synthesized, montaged). Current methods involve simple arithmetic operations conducted on these images, including subtraction or addition, which are non-adaptive in terms of the spatial image content. Therefore, there is a need to improve the comparison module with more sophisticated methods, which are adaptive and which provide better results for subsequent processing and display techniques.

The disadvantages associated with current, imaging systems have made it apparent that a new technique for temporal processing is needed. The new technique should substantially increase accuracy of information acquired obtained from temporal processing. The present invention is directed to this end.

SUMMARY OF INVENTION

In accordance with one aspect of the present invention, a temporal image processing system includes a temporal processing controller adapted to receive a first image signal and a second image signal from a scanning unit. The temporal processing controller comprises a segmentation module adapted to isolate at least one region of interest of the first image signal and the second image signal. The segmentation module is adapted to generate therefrom a segmentation signal. The temporal processing controller further comprises a registration module adapted to receive the segmentation signal and register at least one region of interest. The registration module is further adapted to generate therefrom a registration signal. The temporal processing controller still further comprises a comparison module adapted to receive the segmentation signal and the registration signal. The comparison module generates therefrom an adaptive comparison signal of the first image signal and the second image signal.

In accordance with another aspect of the present invention, a temporal image processing method is provided. The method includes scanning an object and generating a first image signal and a second image signal therefrom. The first image signal and the second image signal are received in a segmentation module. At least one region of interest of the first image signal and the second image signal is isolated. A segmentation signal is also generated and received in a registration module. The at least one region of interest is registered and a registration signal is generated. The segmentation signal and the registration signal are received in a comparison module, and an adaptive comparison signal is generated in response to the segmentation signal and the registration signal.

Additional advantages and features of the present invention will become apparent from the description that follows and may be realized by the instrumentalities and combinations particularly pointed out in the appended claims, taken in conjunction with the accompanying drawings.

BRIEF DESCRIPTION OF DRAWINGS

For a more complete understanding of the invention, there will now be described some embodiments thereof, given by way of example, reference being made to the accompanying drawings, in which.

DETAILED DESCRIPTION

Figure 1:
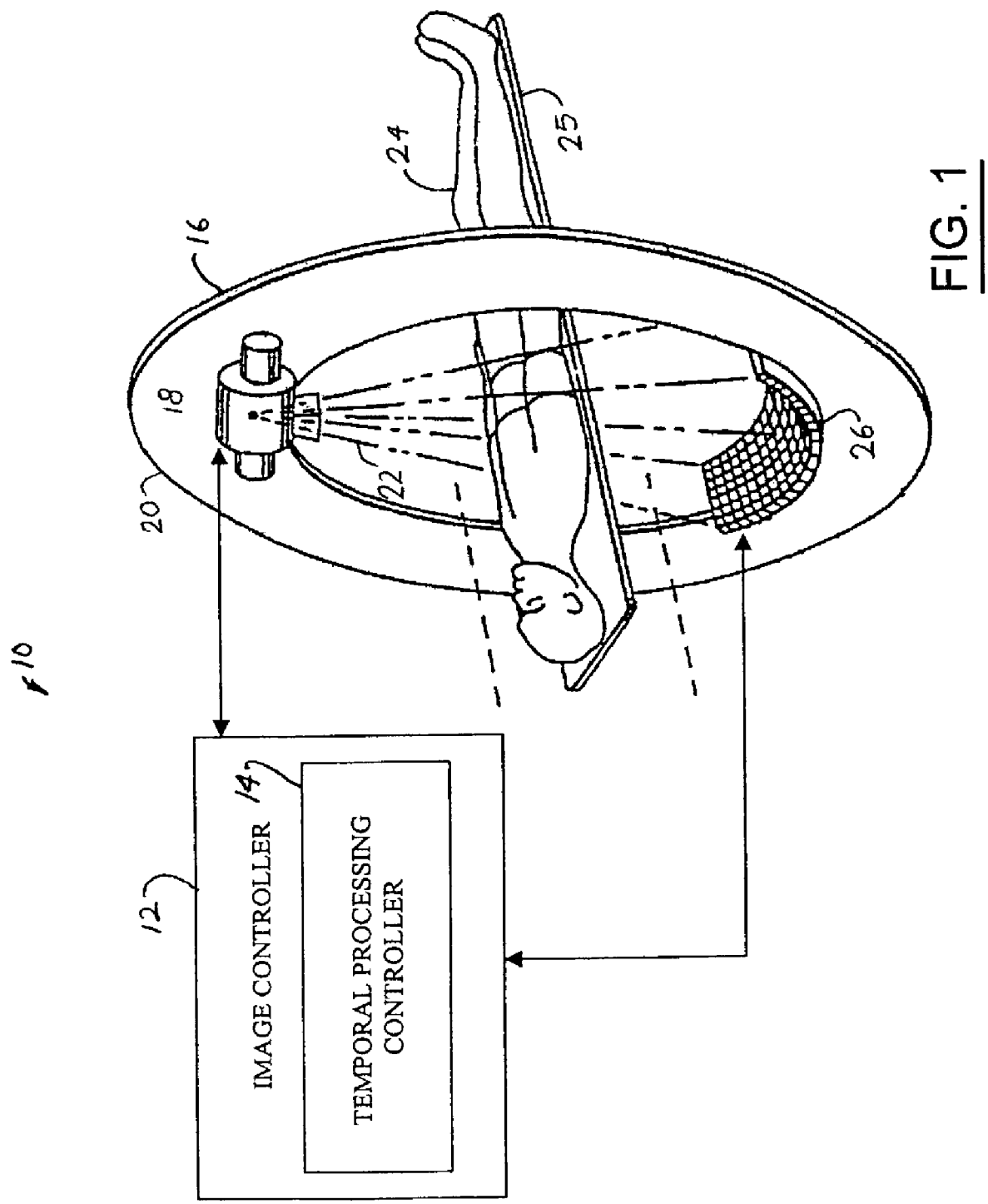
FIG. 1 is a diagram of an imaging system in accordance with an embodiment of the present invention.
Figure 2:
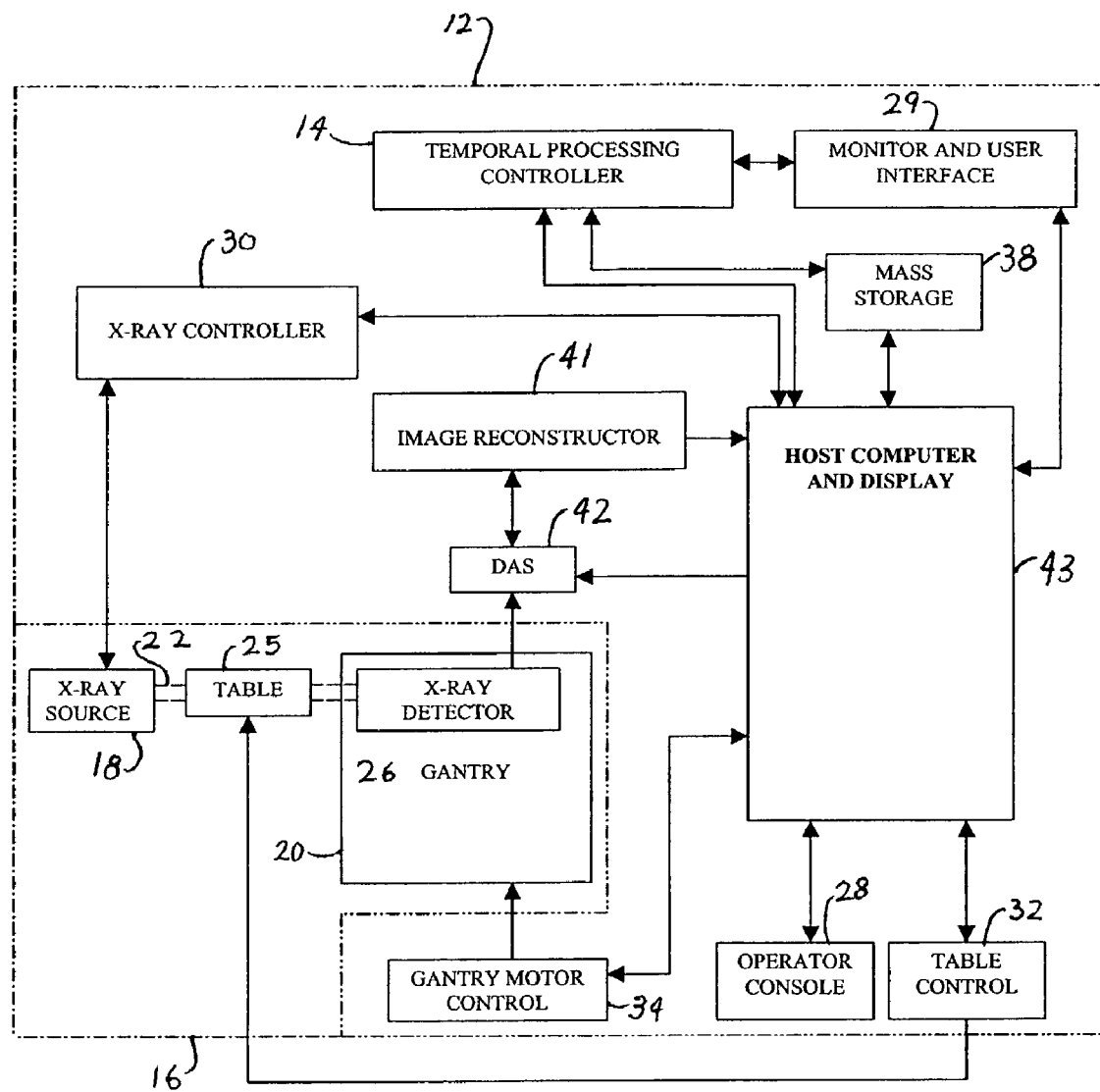
FIG. 2 is a schematic diagram of a portion of FIG. 1.

The present invention is illustrated with respect to a temporal image processing system 10, particularly suited to the medical field. The present invention is, however, applicable to various other uses that may require temporal imaging, as will be understood by one skilled in the art. Referring to FIGS. 1 and 2, an image controller 12, including a temporal processing controller 14, coupled to a scanning unit 16, in accordance with an embodiment of the present invention, is illustrated. The scanning unit 16 includes, for example, an x-ray source 10 coupled to a gantry 20, generating an x-ray flux 22, which passes through an object 24 (e.g. a patient) on a table 15. The system 10 further includes an x-ray detector 26, also coupled to the gantry 20.

The imaging controller 12, including the temporal processing controller 14 and various other widely known imaging control and display components, receives the detector signals and responds by generating a first and a second image signal. The imaging controller 12 also includes, for example, an operator console 28, a monitor and user interface 29, an x-ray controller 30, a table control 32, a gantry motor control 32, a mass storage 38, an image reconstructor 41 and a data acquisition system 42, all of which couple to a host computer and display 43, are well know in the art, and will be discussed later.

Figure 3:
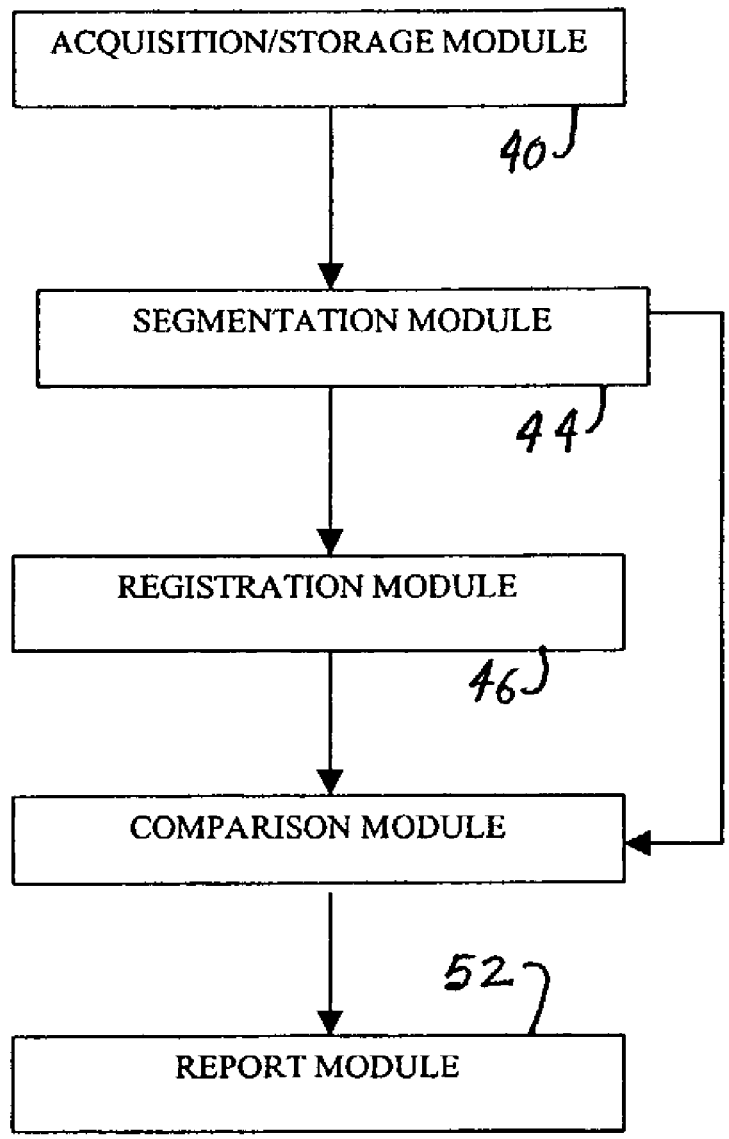
FIG. 3 is a schematic diagram of the temporal processing unit of FIG. 1.

Referring to FIG. 3, a schematic diagram of the temporal processing controller 14 of FIG. 1 is illustrated. One embodiment of the temporal imaging controller includes an acquisition storage module 40, a processing module 42, a segmentation module 44, a registration module 46, a comparison module 50, and a report module 52. The aforementioned modules are either software algorithms or discrete circuit components or a combination thereof, as will be understood by one skilled in the art.

Referring again to FIGS. 1, 2 and 3, the acquisition storage module 40 contains acquired images. For temporal change analysis, a data retrieval system retrieves the data from storage (e.g. the mass storage unit 38) corresponding to an earlier time point or from the image reconstructor 41, which receives signals from the data acquisition system (DAS) 42. The acquisition storage module input images are 1-D, 2-D, 3-D, derived, synthesized, or montaged, such that multiple separate images from a single time point are combined to provide a larger composite, seamless image.

As an illustrative example, only two images S1 and S2 corresponding to two time points $t_1$ and $t_2$ are included, however one skilled in the art will realize that the general approach can be extended for any number of images in the acquisition and temporal sequence. The temporal comparison image is denoted as $S_{1-2}$. S1 and S2 are either the original unprocessed images from an acquisition system or alternately, post-processed versions of the original images. One skilled in the art will realize that the acquisition storage module 40 can include images from almost any digital imaging source.

The segmentation module 44 receives the two images, S1 and S2, from the acquisition storage module 40 and, through automated or manual operation in the user interface 29 or operator console 28, isolates regions of interest between the two x-ray images, S1 and S2. Often the entire image is the region of interest.

A segmentation mask (M) is generated from segmentation module logic, or alternately is input by a scan operator. The segmentation mask (M) is an application-dependent process for isolating at least one region of interest. For example, for 5 areas of interest, each of the 5 areas receives an index number between 1 and 5, for the first image, and a corresponding designation is applied to each of the areas of interest for the second image. All other portions of the object are designated either "0" or in an alternate, known distinguishing manner (e.g. color indexing, etc.), as will be discussed later regarding the comparison module.

The registration module 46 receives the region of interest signals from the segmentation module 44, provides methods of registration and therefrom generates a registration signal. If the regions of interest for temporal change analysis are small, rigid body registration transformations, including translation, rotation, magnification, and shearing, are sufficient to register a pair of images from $t_1$ and $t_2$. If, however, the regions of interest are large, including almost the entire image, warped, elastic transformations are applied.

One way to implement the warped registration is to use a multi-scale, multi-region, pyramidal approach. For this approach, a different cost function highlighting changes is optimized at every scale. Such cost functions are correlation methods, such as mathematical correlation and sign-change measurement, or statistical methods such as entropy measurements and mutual information analysis.

For warped registration, images are re-sampled at a given scale and subsequently divided into multiple regions. Separate shift vectors are calculated for different regions. Shift vectors are interpolated to produce a smooth shift transformation, which is applied to warp one of the images. The images are re-sampled and the warped registration process is repeated at the next higher scale until the pre-determined final scale is reached. In other situations, a combination of rigid registration and elastic transformations is used.

The comparison module 50 receives the segmentation signal and the registration signal and computes a dissimilarity measure between the registered images and therefrom generates a comparison signal. Registered image comparison is performed in several ways. In addition to, or instead of, using a simple subtraction between the registered images to obtain the dissimilarity image, the system includes an enhanced division method, which is described as $(S1*S2)/(S2*S2+\phi)$.

For mono-modality temporal processing, the prior art methods obtain difference image D=S1S2. The present invention includes a method for adaptive image comparison between two images, S1 and S2. An adaptive method includes the following equation: $D1_a=(S1*S2)/(S2*S2+\phi)$, where the scalar constant $\phi>0$. For a degenerative case, $\phi=0$, the above equation becomes a straight division, S1/S2. A more sophisticated method includes $\phi$ as a variable having values set according to a look-up table, as will be understood by one skilled in the art. In an embodiment, the input to the comparison module 50 also includes a segmentation mask (M), generated from the segmentation module 44 or from user input, in addition to S1 and S2. M is obtained from prior knowledge of the specific features in the compared images, such as bone structure or organ type. The segmentation mask guides the comparison results at various locations, as will be understood by one skilled in the art.

For example, the following comparison method depending on spatial attributes: If M>0, $D1_1=(S1*S2)/(S2*S2+\phi)$; Else $D1_a=0$.

A general form of this method is the following: If M=m1, $D1_a=(S1*S2)/(S2*S2+\phi k)$; Else if M=m2, $D1_a=(S1*S2)/(S2*S2+\phi k)$; Else if M=mk, $D1_a=(S1*S2)/(S2*S2+\phi k)$; Else $D1_a=0$.

Where m is a variable designating which index is focused on in the referenced equation, and k is a constant, developed through known testing methods.

The report module 52 receives the comparison signal and provides the display and quantification capabilities for the user to visualize and or quantify the results of temporal comparison. Results of temporal comparisons are simultaneously displayed on a second display unit with either image S1 or S2. Or a superposition of $S_{1-2}$ onto S1 or S2 generates with a logical operator based on pre-specified criterion. For quantitative comparison, color look-up tables for the overlaid images are used. The resulting combination is realized with a multi-color overlay display.

The present invention is illustrated with respect to x-ray and computed tomography (CT) systems, however it is alternately used for any type of imaging system including, magnetic resonance imaging (MRI), mammography, vascular x-ray imaging, bone scanning, positron emission tomography (PED), ultrasound, optical imaging, etc. Further embodiments include non-medical applications such as weld inspection, metal inspection. Essentially, anything that could use an imaging system to make one, two and three dimensional images or one, two, and three dimensional montaged images.

Typical scanning units include an x-ray source 18 coupled to a gantry 20. The x-ray source 18 generates an x-ray flux 22, which passes through a scanned object 26 on a table 25. An x-ray detector 26 is also typically coupled to the gantry 20 such that the detector 26 receives the x-ray flux 22.

The x-ray source 18 is embodied as a flat panel x-ray source or an extended x-ray source (e.g. Imatron), or a standard x-ray tube. The x-ray source 18 is activated by either a host computer 43 or an x-ray controller 30, as will be understood by one skilled in the art. The x-ray source 18 sends the x-ray flux 22 through an object 24 on a moveable table 25 controlled by a table control device 37 acting in response to signals from the host computer 43, as will be understood by one skilled in the art.

The embodied gantry 20 is a ring shaped platform that rotates around the scanned object 24 in response to signals from the gantry motor control 34, as will be understood by one skilled in the art.

For a single image, S1, the x-ray flux 22 from the x-ray source 18 passes through the object 24 and impinges on the x-ray detector 26. Detector specific corrections or calibrations are then engaged, as will be understood by one skilled in the art. The signal then passes to the host computer and display 43, where the signal is converted to a gray level corresponding to the attenuation of an x-ray photon through the patient. The image is then stored in the mass storage unit 38 or received in the temporal imaging controller 14.

The detector 26 is typically located opposite the x-ray source 18 to receive x-ray flux 22 generated therefrom.

The host computer 43 receives detector signals. The host computer 43 also activates the x-ray source 18 through signals from the operator console 28 or user interface 29 however, alternate embodiments include independent activation means for the x-ray source 18. The present invention includes an operator console 28 for control by technicians, as will be understood by one skilled in the art.

One embodiment of the present invention incorporates use of temporal imaging for the scout scan on an imaging system. During a scout scan from the x-ray source 18 to the detector elements 26, the x-ray tube remains stationary while the patient table 25 translates under the x-ray flux 22. This results in a two-dimensional image ideal for qualitative information and for locating the desired position for scanning during further temporal imaging.

Figure 4:
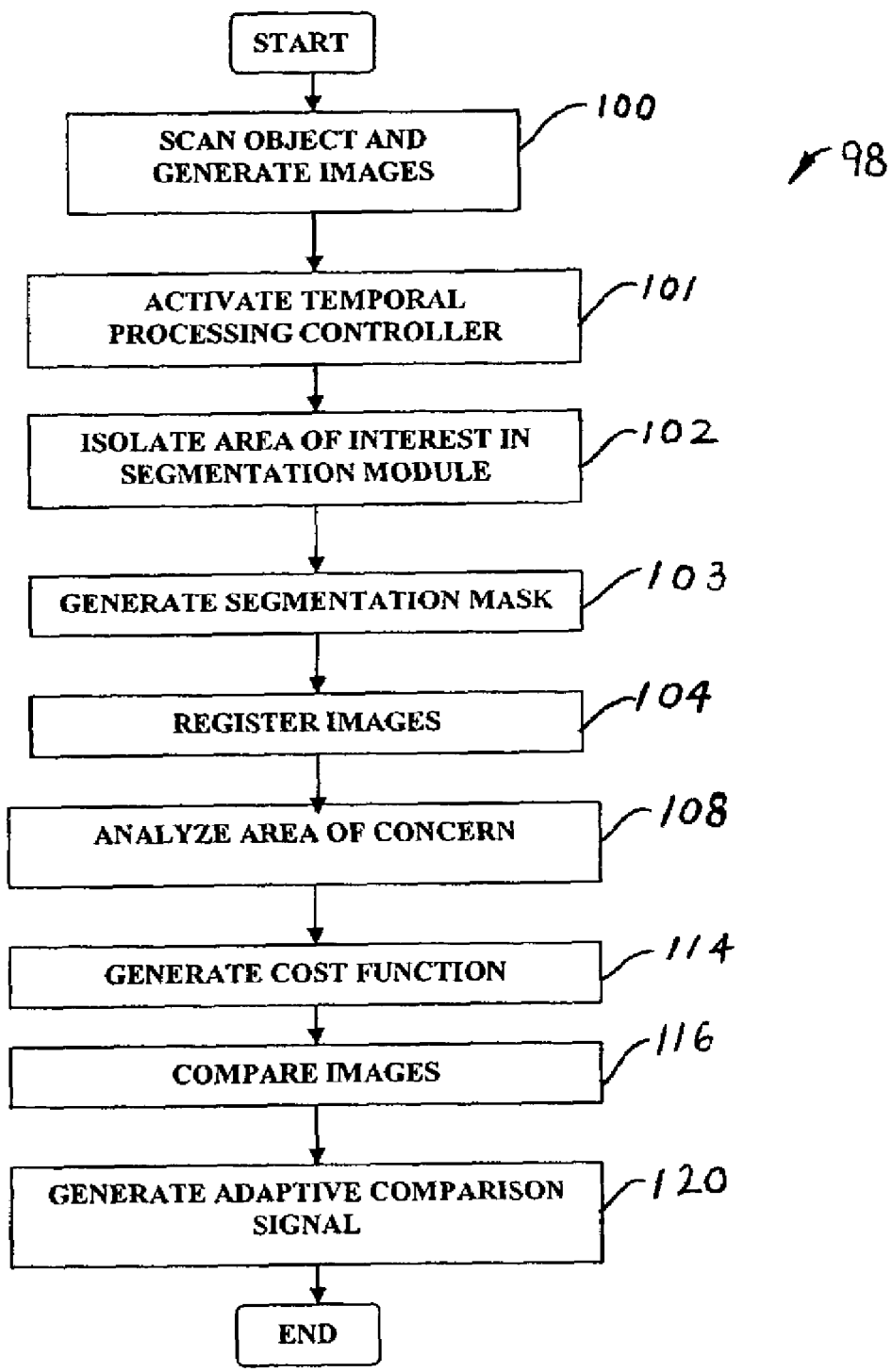
FIG. 4 is a block diagram of a temporal processing method, in accordance with an embodiment of the present invention.

Referring to FIG. 4, a block diagram of a temporal image processing method 98 is illustrated. The logic starts in operation block 100 where the object is scanned at different periods of time to generate image signals.

Operation block 101 then activates, and the temporal processing controller acquires the image signals through the acquisition storage module and generates an acquisition signal containing the image signals.

In operation block 102, the segmentation module receives the acquisition signal and isolates regions of interest. In one embodiment, operation block 103 activates, and the segmentation module generates a segmentation mask, which operates to guide the control results. Alternately, the segmentation mask is input into the temporal processing controller from an outside source, as was previously discussed.

In block 104, the temporal processing controller registers the regions of interest.

In operation block 108 the area of concern is analyzed. A minor region is analyzed with at least one of translation criteria, rotation criteria, magnification criteria, or shearing criteria, thereby generating a cost signal (i.e. cost function or a figure of merit of the cost function) in operation block 114.

For a major area, at least one warped transformation criterion is used, thereby generating a cost signal (i.e. cost function or a figure of merit of the cost function) in operation block 114.

Operation block 116 then activates, and the comparison module receives the segmentation signal, the registration signal and the segmentation mask. The comparison module generates therefrom an adaptive comparison signal in operation block 120. Following the adaptive comparison, the report module receives the comparison signal and provides the display and quantification capabilities for the user to visualize and or quantify the results of temporal comparison.

In operation, the temporal image processing method includes scanning an object and generating a first image signal and a second image signal therefrom. A segmentation module receives the first image signal and the second image signal, isolates at least one region of interest and generates therefrom a segmentation signal. A registration module receives the segmentation signal, registers the region of interest, and generates a registration signal. A comparison module receives the segmentation signal and the registration signal and generates an adaptive comparison signal in response thereto. The comparison module also receives a segmentation mask from the segmentation module or from a user input, which guides the comparison results at various locations.

From the foregoing, it can be seen that there has been brought to the art a new temporal image processing system 10. It is to be understood that the preceding description of the preferred embodiment is merely illustrative of some of the many specific embodiments that represent applications of the principles of the present invention. Numerous and other arrangements would be evident to those skilled in the art without departing from the scope of the invention as defined by the following claims.

The invention claimed is:

1. A temporal processing controller adapted to receive a first image signal and a second image signal from a scanning unit comprises:
    a segmentation module adapted to isolate at least one region of interest of said first image signal and said second image signal, said segmentation module further adapted to generate therefrom a segmentation signal;
    a registration module adapted to receive said segmentation signal and register said at least one region of interest, said registration module further adapted to generate therefrom a registration signal; and
    a comparison module adapted to receive said segmentation signal and said registration signal, said comparison module further adapted to generate therefrom an adaptive comparison signal of said first image signal and said second image signal, wherein said comparison module further adapted to generate said adaptive comparison signal of said first image signal and said second image signal through an enhanced division method including, $(S_1 * S_2)/(S_2 * S_2 + \phi)$.

2. The system of claim 1 wherein said scanning unit is adapted to scan an object and generate said first image signal and said second image signal from said object; and
    wherein the system comprises an image controller coupled to said scanning unit and adapted to receive said first image signal and said second image signal.

3. The system of claim 1, wherein for said region of interest comprising a minor region of said object, at least one rigid body registration transformation, including at least one of translation, rotation, magnification, or shearing, is a criterion used to register said first image signal and said second image signal.

4. The system of claim 1, wherein for said region of interest including a major region of said object, at least one warped transformation is a criterion used to register said first image signal and said second image signal.

5. The system of claim 4, wherein said at least one warped transformation is implemented through multi-region, multi-scale, pyramidal logic designed such that a different cost function is adapted to highlight changes between said first image signal and said second image signal at each of a plurality of scales.

6. The system of claim 5, wherein said cost function includes at least one of mathematical correlation, sign-change measurement, or statistical analysis.

7. The system of claim 1, wherein said first image is one of a one-dimensional, a two-dimensional image, a three-dimensional image, a one-dimensional montage image, a two-dimensional montage image, or a three-dimensional montage image.

8. The system of claim 1, wherein said comparison module is further adapted to receive a segmentation mask signal based on at least one known feature of said first image signal, said segmentation mask being generated from at least one of said segmentation module or a user input.

9. A temporal image processing method comprising:
scanning an object and generating a first image signal and a second image signal therefrom;
receiving said first image signal and said second image signal in a segmentation module;
isolating at least one region of interest of said first image signal and said second image signal;
generating a segmentation signal;
receiving said segmentation signal in a registration module;
registering said at least one region of interest, wherein registering further comprises registering a major region of interest of said object within said first image signal and said second image signal through at least one warped transformation criterion including multi-region, multi-scale, pyramidal logic, wherein the method comprises highlighting changes between said first image signal and said second image signal with a different cost function at each of a plurality of scales;
generating a registration signal;
receiving said segmentation signal and said registration signal in a comparison module; and
generating an adaptive comparison signal in response to said segmentation signal and said registration signal.

10. The method of claim 9 wherein generating a segmentation signal further comprises generating a first image signal including a one-dimensional, two-dimensional image, a three-dimensional image, a one-dimensional montage image, a two-dimensional montage image, or a three-dimensional montage image.

11. The method of claim 9 wherein registering further comprises registering a minor region of interest of said object within said first image signal and said second image signal with at least one of translation criteria, rotation criteria, magnification criteria, or shearing criteria.

12. The method of claim 9 wherein registering further comprises registering a major region of interest of said object within said first image signal and said second image signal through at least one warped transformation criterion.

13. The method of claim 9, wherein said cost function includes at least one of mathematical correlation, sign-change measurement, or statistical analysis.

14. The method of claim 9 wherein receiving said segmentation signal and said registration signal in a comparison module further comprises receiving a segmentation mask signal, based on at least one known feature of said first image signal, in said comparison module.

15. A temporal image processing system comprising:
a scanning unit adapted to scan an object and generate a first image signal and a second image signal of said object; and
an image controller coupled to said scanning unit and adapted to receive said first image signal and said second image signal,
said image controller comprising a temporal processing controller adapted to receive said first image signal and said second image signal in a segmentation module, isolate at least one region of interest of said first image signal and said second image signal, generate a segmentation signal, receive said segmentation signal in a registration module, register said at least one region of interest, generate a registration signal, receive said segmentation signal and said registration signal in a comparison module, and generate an adaptive comparison signal in response to said segmentation signal and said registration signal, wherein for said region of interest including a major region of said object, at least one warped transformation is a criterion used to register said first image signal and said second image signal, wherein said at least one warped transformation is implemented through multi-region multi-scale, pyramidal logic designed such that a different cost function is adapted to highlight changes between said first image signal and said second image signal at each of a plurality of scales.

16. The system of claim 15, wherein said scanning unit comprises one of a CT scanning unit, a positron emission tomography unit, an x-ray scanning unit, an MRI scanning unit, an optical imaging unit, or ultrasound.

17. The system of claim 15, wherein said comparison module is further adapted to receive a segmentation mask signal based on at least one known feature of said first image signal, said segmentation mask being generated from at least one of said segmentation module or a user input.

18. The system of claim 15, wherein said comparison module further adapted to generate said adaptive comparison signal of said first image signal and said second image signal through an enhanced division method including, $(S1*S2)/(S2*S2+\phi)$.

* * * * *